United States Patent [19]

Iinuma

[11] 4,373,533
[45] Feb. 15, 1983

[54] ULTRASONIC DIAGNOSING APPARATUS

[75] Inventor: Kazuhiro Iinuma, Yaita, Japan

[73] Assignee: Tokyo Shibaura Denki Kabushiki Kaisha, Japan

[21] Appl. No.: 237,655

[22] Filed: Feb. 24, 1981

[30] Foreign Application Priority Data

Feb. 27, 1980 [JP] Japan ................... 55-22670

[51] Int. Cl.$^3$ ............................. A61B 10/00
[52] U.S. Cl. .................. 128/663; 73/861.25
[58] Field of Search ............. 128/663; 73/861.25

[56] References Cited

U.S. PATENT DOCUMENTS

| | | | |
|---|---|---|---|
| 3,888,238 | 6/1975 | Meindl et al. | 128/2 V |
| 3,939,707 | 2/1976 | Kossoff | 73/194 A |
| 4,062,237 | 12/1977 | Fox | 128/663 X |
| 4,103,679 | 8/1978 | Aronson | 128/663 |
| 4,141,347 | 2/1979 | Green et al. | 128/663 |
| 4,217,909 | 8/1980 | Papadofrangakis et al. | 128/663 |

OTHER PUBLICATIONS

IEEE Transactions on Sonics and Ultrasonics, Jul. 1970, pp. 170-185.

*Primary Examiner*—Kyle L. Howell
*Assistant Examiner*—Francis J. Jaworski
*Attorney, Agent, or Firm*—Finnegan, Henderson, Farabow, Garrett & Dunner

[57] ABSTRACT

An ultrasonic diagnosing apparatus comprising, a first transducer array having a plurality of ultrasonic transducers arranged in a given direction for transmitting an ultrasonic beam into a tissue of a human body and for receiving the ultrasonic echo reflected from the tissue, a second transducer array having a plurality of ultrasonic transducers, for transmitting an ultrasonic beam into the tissue and receiving the ultrasonic echo reflected from the tissue, arrayed in a direction orthogonal to the direction of an array of the transducers in said first transducer array and arranged at an acute angle with respect to said first transducer array in a direction along which the ultrasonic beam of said first transducer array is transmitted and the ultrasonic echo is received, a first signal processing circuit for processing the ultrasonic echo received by said first transducer array to produce an output signal corresponding to tomogram information of the tissue, a second signal processing circuit for processing the ultrasonic echo received by said second transducer array to produce an output signal corresponding to a velocity of a blood flow in the tissue, first display means for displaying a tomogram based on the output signal of said first signal processing circuit; and second display means for displaying blood flow information based on the output signal of said second signal processing circuit.

6 Claims, 9 Drawing Figures

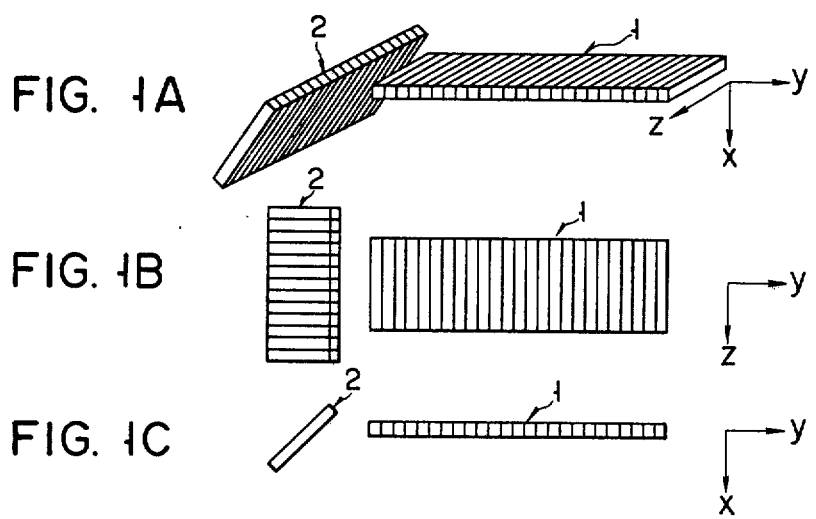
FIG. 1A
FIG. 1B
FIG. 1C
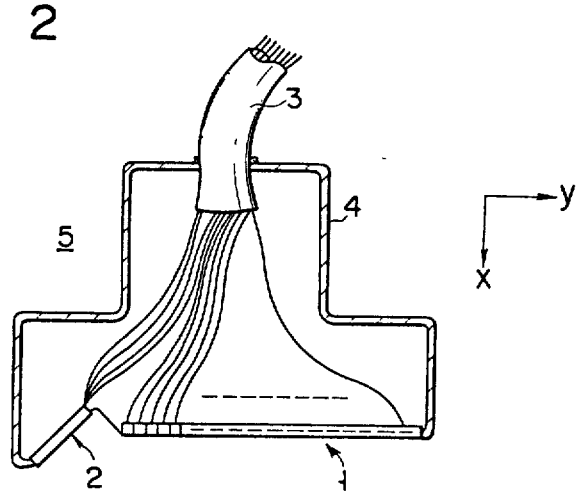
FIG. 2

ULTRASONIC DIAGNOSING APPARATUS

The present invention relates to an ultrasonic diagnosing apparatus which can provide a tomogram by using a ultrasonic linear scanning system and can measure a velocity and a flow rate of a blood flow with a high accuracy.

There has been known an apparatus for measuring a velocity of a blood flow at a specific location in a heart by using an ultrasonic apparatus of sector scanning system and an ultrasonic Doppler apparatus.

A linear scanning system is well adapted for the abdominal diagnosis. In a clinical diagnosis, there is frequently required to measure a velocity and/or a flow rate of the blood flow in order to diagnose an abdomen with a high accuracy. For this reason, it has been desired to develop an ultrasonic diagnosing apparatus of linear scanning system which can measure the velocity and flow rate of the blood flow with a high accuracy and easiness of handling.

Accordingly, an object of the present invention is to provide an ultrasonic diagnosing apparatus of a linear scanning system which can provide a tomogram under examination and can measure a velocity, a flow rate of a blood flow and a two-dimensional distribution of the blood flow flowing through a blood vessel with a high accuracy and easiness of handling.

According to the present invention, there is provided an ultrasonic diagnosing apparatus comprising: a first transducer array having a plurality of ultrasonic transducers arrayed in a given direction for transmitting an ultrasonic beam into a tissue of a human body and for receiving the ultrasonic echo reflected from the tissue; a second transducer array having a plurality of ultrasonic transducers, for transmitting an ultrasonic beam into the tissue and receiving the ultrasonic echo reflected from the tissue, arrayed in a direction orthogonal to the direction of an array of the transducers in the first transducers array and arranged at an acute angle with respect to the first transducer array in a direction along which the ultrasonic beam of the first array is transmitted and the ultrasonic echo is received; a first signal processing circuit for processing the ultrasonic echo received by said first transducer array to produce an output signal corresponding to tomogram information of the tissue; a second signal processing circuit for processing the ultrasonic echo received by said second transducer array to produce an output signal corresponding to a velocity of a blood flow in the tissue; first display means for displaying a tomogram based on the output signal of said first signal processing circuit; and second display means for displaying blood flow information based on the output signal of said second processing circuit.

The present invention will be better understood when carefully reading the following description taken in connection with the accompanying drawings, in which:

FIGS. 1A to 1C show a construction and an arrangement of first and second transducer arrays and assembled into a probe used in an ultrasonic diagnosing apparatus according to the present invention, FIG. 1A shows a perspective view of the combination of the transducer arrays and when those are assembled into the probe, FIG. 1B is a plan view of the transducer arrays, and FIG. 1C is a front view of the transducer arrays;

FIG. 2 is a longitudinal sectional view of an ultrasonic probe using the transducer arrays shown in FIGS. 1A to 1C;

As shown in FIGS. 1A to 1C, the transducer arrays 1 and 2 respectively comprises 64 and 32 ultrasonic transducers arrayed in given directions. Each transducer has a width of 1 mm, a length of 10 mm, and a resonance frequency of 5 MHz. A length of the first transducer array 1 as viewed in a direction of the array (referred to as an array length) is 64 mm, and an array length of the second transducer array is 32 mm. The second transducer array 2 is disposed substantially orthogonal to the direction of the array length of the first transducer array 1.

Figure 3A:
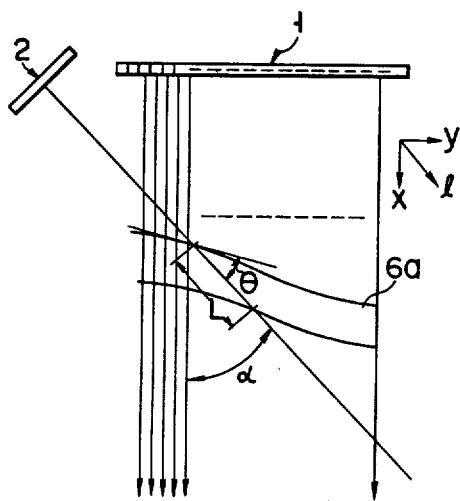
FIGS. 3A and 3B illustrate the ways of scanning of the ultrasonic beams radiated by the transducer arrays shown in FIGS. 3A and 3B.
Figure 3B:
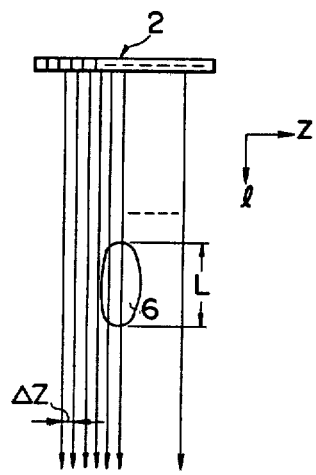

The transducers of the transducer arrays 1 and 2 are connected to an electronic drive circuits (to be described later) by lead wires. Those lead wires are gathered into a cable 3 as shown in the drawing of FIG. 2. The arrays 1 and 2 and the cable 3 are fixed to a casing 4 to form an ultrasonic probe 5. In use, the transducer arrays 1 and 2 of the probe 5 are placed on a surface of a human body. The transducers 1 and 2 receive drive pulses from the electronic circuit to transmit ultrasonic beams toward the tissue of the human body and to receive the ultrasonic echos reflected from the tissue. The direction of the ultrasonic beam radiated from the first transducer array 1 is an X direction (FIGS. 1A and 1C) and that of the second transducer array 2 is an l direction i.e. a direction orthogonal to a Z-direction but in parallel with an X-Y plane (FIG. 1C). The direction along which the second transducer array 2 transmits the ultrasonic beam into the tissue defines an acute angle $\alpha$ (FIG. 3A) with respect to that of the first transducer array 1. The directions of the ultrasonic beams are illustrated in details in FIGS. 3A and 3B. FIG. 3A illustrates the directions of the ultrasonic beams radiated from the arrays 1 and 2, which are in the X-Y plane, together with a first B mode tomogram (a first B mode image) 6a of a longitudinal section of a blood vessel, when the probe 5 is placed on a surface of a human body so that the blood vessel is located in the scanning area of the probe 5. As illustrated in FIG. 3A, the ultrasonic beam of the transducer array 1 is transmitted along the X direction. The ultrasonic beam of the transducer array 2 is transmitted in parallel with the X-Y plane and is at the acute angle $\alpha$ with respect to the direction of the ultrasonic beam of the transducer array 1. FIG. 3B illustrates the direction of the ultrasonic beam radiated from the second transducer array 2, which is in the Z-l plane, together with a second B mode tomogram (a second B mode image) 6b of a cross section of the blood vessel.

In FIG. 3A, $\theta$ is an angle between the ultrasonic beam of the second array 2 and a tangential direction at a point of the blood vessel where the ultrasonic beam of the second array 2 crosses the blood vessel. In FIGS. 3A and 3B, a symbol L designates the maximum length of the tomogram 6a as viewed in the direction along which the second array 2 radiates the ultrasonic beam. In FIG. 3B, "ΔZ" designates an interval between the adjacent scanning lines, each of which is indicative of a resultant intensity of ultrasonic beams concurrently radiated from the second array 2 to form the second B mode tomogram 6b.

The operation of the ultrasonic diagnosing apparatus with the probe 5 as mentioned above will be described referring FIG. 4 illustrating in block diagram a circuit construction of the ultrasonic diagnosing apparatus.

Figure 4:
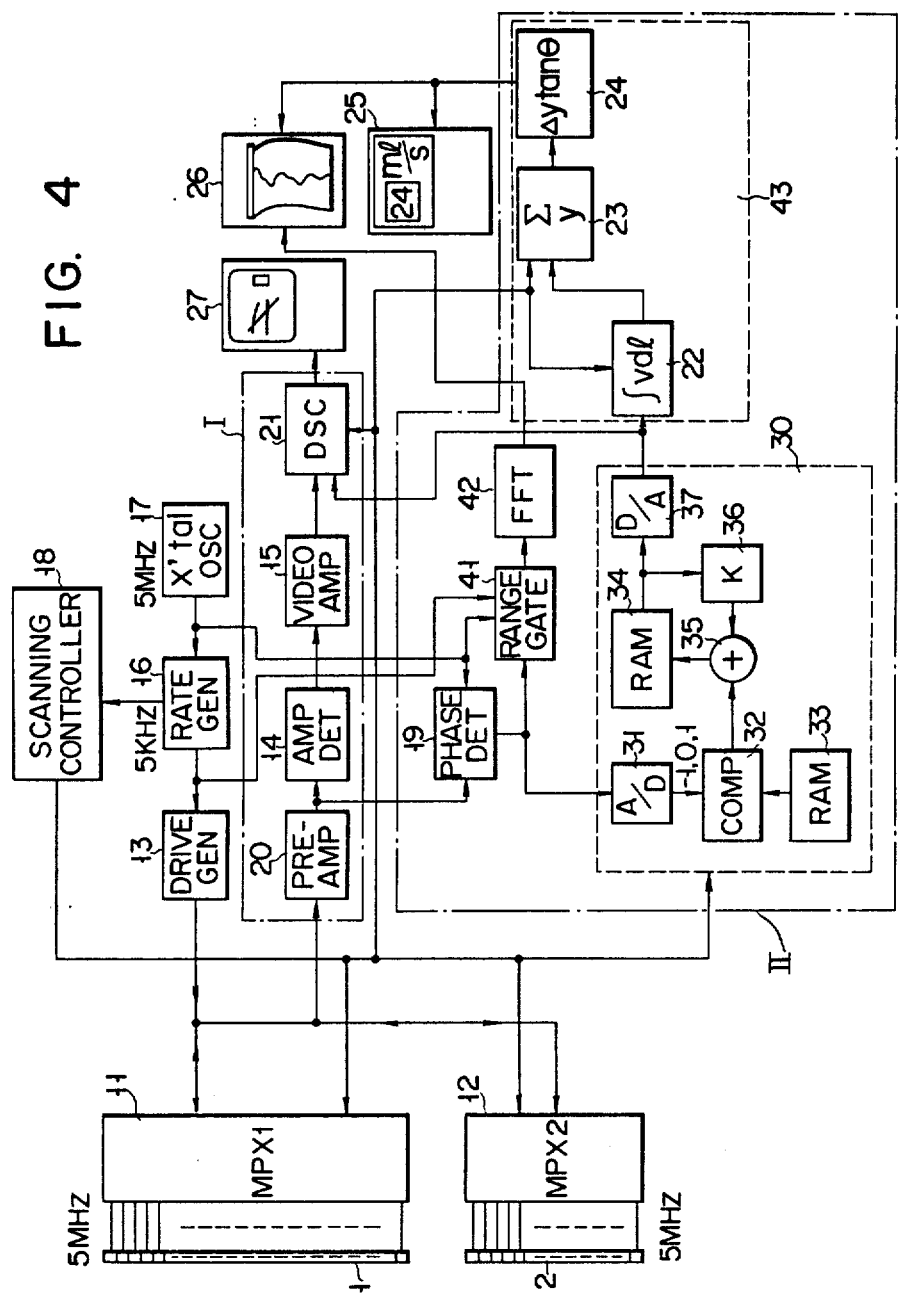
FIG. 4 is a block diagram of an embodiment of the ultrasonic diagnosing apparatus according to the present invention.

In FIG. 4 a crystal oscillator 17 stably generates a reference pulse signal of 5 MHz, for example. A rate pulse generator 16 divides the output frequency signal of the generator 17 to produce rate pulses of 5 KHz, for example. A drive pulse generator 13 receives the output pulse of the rate pulse generator 16 and produces a drive pulse in synchronism with the rate pulse. The output pulse of the drive pulse generator 13 is applied through specific channels of multiplexers 11 and 12 to corresponding specific transducers of the first and second transducer arrays 1 and 2 to drive those transducers to emit ultrasonic beams therefrom. Switching control of the channels of the multiplexers 11 and 12 is performed by a scanning controller 18 which operates in response to the rate pulse of the rate pulse generator 16. Specifically, 8 channels, for example, continuously arranged of those channels in each multiplexers 11 and 12 are grouped into one to be driven. When receiving the rate pulse, the scanning controller 18 simultaneously turns on the one group of the channels. In response to the next rate pulse, the scanning controller 18 turns on the next group of the channels which is shifted by one channel from the preceeding channel group. In this way, the subsequent groups of the channels are turned on by the scanning controller 18. When one of the channel groups of the multiplexer 11 is turned on, the channels of the multiplexer 12 are all turned off. On the other hand, when one of the channel groups in the multiplexer 12 is turned on, the channels of the multiplexer 11 are all turned off.

For the sake of explanation, the imaging of the first B mode tomogram 6a of a blood vessel by the first transducer array 1 will first be discussed and then that of the second B mode tomogram 6b by the second transducer array 2 will follow.

The scanning controller 18, when receiving a first rate pulse of the rate pulse generator 16, controls the multiplexer 11 so as to turn ON the first eight channels of the multiplexer 11. At this time, the first rate pulse is applied to the drive pulse generator 13 which in turn produces a drive pulse. The drive pulse of the generator 13 is applied through the first eight channels to the transducers of the first transducer array 1 which are respectively connected to these channels. When receiving the drive pulse, those eight transducer elements radiate an ultrasonic beam. In use of the ultrasonic diagnosing apparatus, the probe 5 is placed on a human body so that the transducer arrays 1 and 2 are in contact with a surface of the body. Accordingly, the ultrasonic beam of the transducer array 1 propagates in the x direction within the blood vessel in FIG. 3A. Those eight transducers receive the ultrasonic echoes reflected from the blood vessel and convert the same into electrical signals. The electrical signals are applied through the multiplexer 11 to a signal processing circuit I as an image signal corresponding to the first scanning line for the first B mode tomogram 6a. The first ultrasonic beam for obtaining the image signal corresponding to the first scanning line will be expressed by IB1 hereinafter. The signal processing circuit I in the embodiment comprises a preamplifier 20, an amplitude detector 14, a video amplifier 15 and a digital scan converter 21. The preamplifier 20 functions as a buffer amplifier for the image signal supplied from the multiplexer 11. The output signal of the preamplifier 20 is supplied to the amplitude detector 14 where an amplitude thereof is detected. The output signal of the amplitude detector 14 is supplied to the video amplifier 15 where it is amplified. The amplified signal is then supplied to the digital scan converter (DSC) 21. The DSC 21 may include an A/D converter, an input buffer memory, a random access memory, an output buffer memory, a D/A converter and a timing control circuit to scan-convert the input signal of the DSC 21 into a television video signal, for example, substantially on a real time basis, which in turn is supplied to a TV monitor 27 as an intensity modulation signal for a first B mode tomogram 6A. Therefore, the image signal corresponding to the first scanning line is stored in the random access memory of the DSC 21 under control of the scanning controller 18.

When the probe 5 receives the second rate pulse, the scanning controller 11 turn on the second eight channels, i.e. the second to ninth channels, of the multiplexer 11. Accordingly, the output drive pulse of the drive pulse generator 13 is applied to the second to ninth transducers of the first array 1, through the second eight channels. Upon receipt of the drive pulse, the eight transducers radiate a second ultrasonic beam. Then the image signal corresponding to the second scanning line for the first B mode tomogram 6a is obtained through signal processing similar to the first scanning line. The second ultrasonic beam for obtaining the image signal corresponding to the second scanning line will be expressed by IB2. The image signal is stored in the random access memory of the DSC 21. The timing control of the DSC 21 is performed in response to the output pulse of the scanning controller 18. For the third, fourth, and subsequent rate pulses applied, the channels to be turned on are subsequently shifted by one channel to obtain the image signals corresponding to the scanning lines which are stored in the random access memory of the DSC 21, respectively. The image signals stored in the random access memory of DSC 21 are read out in a TV format under the control of the scanning controller 18 and are supplied to the TV monitor 27 which in turn displays the first B mode tomogram 6a of the blood vessel, as shown in FIG. 3A. In this case, a linear marker for indicating a direction of an ultrasonic beam by the second array 2 is also displayed on the screen of the TV monitor 27, as shown in FIG. 3A.

Switching operation of the multiplexer 12 is similarly controlled by the scanning controller 18. In response to the respective rate pulses, image signals corresponding to first, second, . . . scanning lines for the second B mode tomogram 6b of the blood vessel are obtained and stored in the random access memory of the DSC 21, after signal processing through the preamplifier 20, the amplitude detector 14 and the video amplifier 15. The image signals stored in the random access memory of the DSC 21 are, as in the case of those of the first B made tomogram 6a, read out in a TV format under the control of scanning controller 18 and are supplied to the TV monitor 27. In this way, the first and second B mode tomograms 6a and 6b of the blood vessel are displayed side by side on the screen of the TV monitor 27.

The first, second, ... ultrasonic beams for obtaining the image signals corresponding to the first, second, ... scanning lines for the second B mode tomogram 6b will be denoted as IIB1, IIB2, ..., respectively. The second B mode tomogram 6b of the blood vessel obtained by the second array 2 is as shown in FIG. 3B. The second B mode tomogram 6b is vertical to the first B mode tomogram 6a shown in FIG. 3A and is inclined at the acute angle α with respect to the direction of the ultrasonic beam of the array 1.

The number of scanning lines (ultrasonic beams) for forming the first B mode tomogram 6a is 57 (=64−8+1). The number of scanning lines (ultrasonic beams) for forming the second B mode tomogram 6b is 25 (=32−8+1).

A second signal processing circuit II for forming the blood flow information by using the Doppler pulses will be described hereinafter.

For this signal processing, the scanning controller 18 turns on the (i)th, (i+1)th, ... (i+7)th channels of the multiplexer 12, (i=1, 2, ..., 25), while turns off the remaining channels of the multiplexer 12. The output pulse produced by the drive pulse generator 13 in response to the first rate pulse is applied through the (i)th, (i+1)th, ... (i+7)th channels to the (i)th, (i+1)th, ... (i+7)th transducers to drive those transducers. These transducers then radiate an ultrasonic beam for Doppler signal detection into the human body towards the blood vessel and receives the ultrasonic echo reflected from the blood vessel. The ultrasonic echo is converted into an electrical signal by the transducers, and then supplied through the multiplexer 12 to the preamplifier 20 where it is amplified. The output signal of the preamplifer 20 is supplied to a phase detector 19. For the second, third, and subsequent rate pulses, the same channels, the (i)th to (i+7)th, are turned on and, thus, the position where the ultrasonic beams for Doppler signal detection are radiated is fixed. The ultrasonic beam for the Doppler signal detection is denoted as IIDi. As explained above, when the channels of the multiplexer 12 are turned on, the channels of the multiplexer 11 are turned off.

The output signal of the preamplifier 20 is supplied to a phase detector 19 where it is multiplied by a pulse signal of 5 MHz, for example, issued from the crystal oscillator 17. Sampling of the output signals of the phase detector 19 is carried out in a given period between adjacent rate pulses. When the sampled signals are supplied to a zero-crossing ratemeter, the ratemeter produces an output signal which represents a velocity of the blood flow at a given position spaced from the ultrasonic beam radiating/receiving surface of the array 2. The distance between the surface of the array 2 and the position corresponds to the period during which the output signals of the phase detector 19 are sampled. This system of detecting the velocity of the blood flow is similar to the system used in an ultrasonic Doppler blood flow meter comprising a conventional zero-crossing ratemeter.

In this embodiment, however, velocities of the blood flow at various positions through which the ultrasonic beam passes can simultaneously be measured. In this embodiment, to make the measurement, the output signal of the phase detector 19 is supplied to an analog to digital (A/D) converter 31 in a blood flow velocity detecting circuit 30. The A/D converter 31 converts the output signal of the phase detector 19 into zero-crossing digital data. The zero-crossing data include a sign bit in addition to two binary bits "1" and "0." The frequency of a clock pulse signal for timing supplied to the A/D converter 31 is selected to be 128 times that of the rate pulse signal, for example. This indicates that the echo information obtained during one rate pulse is segmented into 128 units.

A random access memory (RAM) 33 has 128 addresses corresponding to the 128 units. The information stored in the memory location of each address may take a form of "1," "0" or "−1." The addresses may have all "1" as their initial values. For each rate pulse, a comparator 32 compares the 128 output signals from the A/D converter 31 with the corresponding output signals from the RAM 33. When the output signals from the A/D converter 31 and the RAM 33 are different from each other, that is, "1" and "−1" or "−1" and "1," respectively, the comparator 32 produces "1" signal and inverts the sign of the contents in the corresponding address of the RAM 33. When the output signals of the A/D converter 31 are, respectively, 1(0), 2(1), 3(−1), 4(1), 5(0), ..., 128(1), the contents of the third address, for example, is changed from "−1" to "1." The output signal of the comparator 32 is applied to an adder 35 where it is added to the output signal from a coefficient multiplier 36 having a coefficient of K times. The resultant data of the addition is loaded into a corresponding address of the RAM 34 which can store the data of 8 bits, for example. The output signal of the RAM 34 is applied through the coefficient multiplier 36 of K times (K=127/128, for example) to the adder 35. The output signal of the RAM 34 is taken out as an analog signal representing a velocity of the blood flow from the blood flow velocity detecting circuit 30 through a D/A converter 37. The circuit including the adder 35, the RAM 34 and the coefficient multiplier 36 corresponds to an integrating circuit including a capacitor and resistor in the version of an analog circuit. The circuit independently integrates 128 data for each rate in a synchronizing manner, so that the D/A converter 37 produces blood flow velocity signals corresponding to 128 segments simultaneously.

The output signals of the D/A converter 37 are supplied to an integrator 22 where those signals are integrated with respect to the l direction. The output signal of the integrator 22 is Vi cos θ dl. A flow rate Q of the blood flow is the result of the integration of the blood flow velocity Vi with respect to a cross section of the blood vessel orthogonal to the axis of the blood vessel. The blood flow rate is expressed by $$Q = \Delta Z \sum_{i=1}^{n} [Vi\sin\theta \, dl] \quad (1)$$

where ΔZ designates an interval between the adjacent scanning lines, each of which is indicative of a resultant intensity of ultrasonic beams concurrently radiated from the second array 2, Vi is a velocity of the blood flow in a direction parallel to the blood vessel at a position of the blood vessel for receiving the ultrasonic beam IIDi, and n is the number of scanning lines which pass through a cross section of the blood vessel, where the blood flows at a velocity to be measured.

Then, the output of the integrator 22 is supplied to an adder 23 and then the output signal i.e. the result of the addition of the adder 23 is supplied to the coefficient multiplier 24 where it is multiplied by a given coefficient. The output signal of the coefficient multiplier 24 is given by $$\Delta Z \tan\theta \sum_{i=1}^{n} [Vi\cos\theta \, dl] = \Delta Z \sum_{i=1}^{n} [Vi\sin\theta \, dl] \qquad (2)$$

In this way, the coefficient multiplier 24 produces the data representing the blood flow rate on real time. The flow rate data is supplied to a recorder 26 or a digital display device 25 where it is recorded or displayed.

The range gate circuit 41 receives the output signal of the phase detector 13 to sample a blood flow signal corresponding the ultrasonic echo reflected from the blood vessel under examination. The blood flow signal is sampled and held in the range gate circuit 41 and, then, supplied to a Fourier transformer 42 where it is Fourier-analyzed and its waveform is recorded in the recorder 26. The integrator 22, the adder 23 and the coefficient multiplier 24 cooperate to form a blood flow detecting circuit 43.

Figure 5:
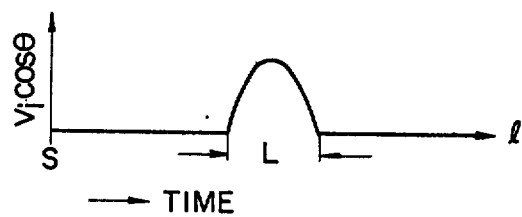
FIG. 5 is a graphical representation of a blood flow velocity of the ultrasonic diagnosing apparatus shown in FIG. 4.

Turning now to FIG. 5, there is illustrated an output signal of the D/A converter 37, or a blood flow velocity characteristic. In the graph of FIG. 5, the ordinate represents Vi cos θ which is proportional to the output signal of the converter 37. The abscissa represents time or distance from the ultrasonic beam transmitting-/receiving surface of the second transducer array 2 along the l direction in FIGS. 3A and 3B. S denotes a position of the beam transmitting/receiving surface of the second array 2. The velocity of the blood flow in the center of the blood vessel is higher than that in the periphery thereof. Therefore, the output signal of the converter 37 takes a waveform of which the amplitude increases toward the center of the vessel as shown in FIG. 5.

When the channesl turned ON for each rate pulse in the multiplexer 12 are shifted by one channel and the corresponding transducers are shifted by one transducer, the ultrasonic beam is shifted by one transducer in the Z direction so that the position where the velocity of the blood flow is to be measured is shifted by one transducer in the Z direction. The ultrasonic beam to obtain the blood flow information obtained by shifting the transducers by one transducer will be denoted as IID(i+1).

Figure 6:
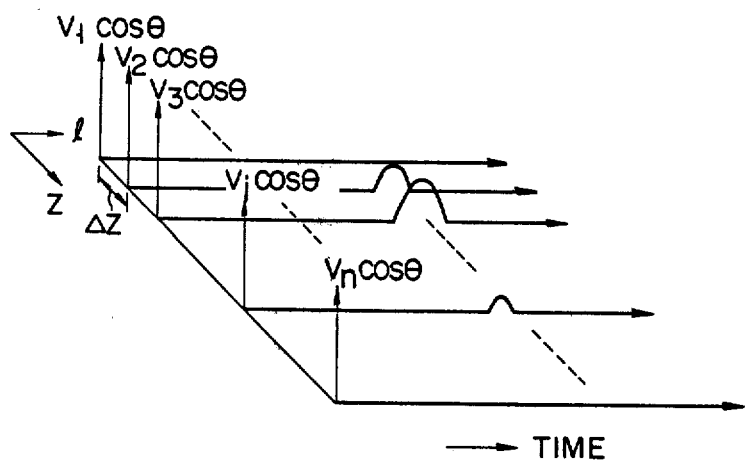
FIG. 6 illustrates a distribution of the blood flow velocity in an l-Z plane.

FIG. 6 illustrates an arrangement of the blood flow velocity characteristics shown in FIG. 5 with respect to the Z direction. For displaying this arrangement of the characteristics, the output signals of the D/A converter 37 are also supplied to and stored in the DSC 21 and are read out and displayed by the TV monitor 27 under the control of the scanning controller 18. The arrangement of the velocity characteristics shown in FIG. 6 is very useful for checking a distribution of the blood flow.

The B mode tomograms and the blood flow information are separately obtained according to the process are mentioned above. Description will be given about a process to simultaneously obtain both the information.

Firstly, the probe 5 is disposed in contact with a surface of a human body and the B mode tomograms 6a and 6b of a blood vessel are displayed on the screen of the CRT display device 27, through the operation as mentioned above. In this case, the ultrasonic beams are radiated in the order of, for example IB1, IB2, IIB1, IB3, IB4, IIB2, . . . IIB25, IB51, IB52, ( ), IB53, IB54, ( ), IB55, IB56, ( ), IB57, ( ), ( ), IB1, IB2, . . . . In this order, the contents parenthesized may be any ultrasonic beam.

An ultrasonic beam for Doppler signal detection is set at the center of the first B mode tomogram 6a of the blood vessel. Under this condition, the ultrasonic beam for obtaining the second B mode tomogram 6b and the ultrasonic beam for obtaining the Doppler signal are alternately radiated. If the beam at the center of the blood vessel as viewed in the length direction is the "j"th one, the beams are radiated in the order of IIB1, IIDj, IIB2, IIDj, . . . IIB25, IIDj, IIB1, IIDj, . . . . In this case, the output signal of the phase detector 19 is used only for the radiation of the beam IIDj.

Under this condition, if the beam for the B mode tomogram 6b is stopped while the beam for Doppler signal detection alone is radiated, that is to say, the beam for Doppler signal detection is repititively radiated IIDj, IIDj, . . . IIDj, . . . , there is not produced the noise arising from the ultrasonic beams IIB1, IIB2, . . . IIB25 and therefore a Doppler blood flow signal with an excellent S/N ratio can be obtained. In this case, the position for radiating the ultrasonic beam for Doppler signal detection is fixed at a point for any rate. It is therefore possible to detect the blood flow only at the center in the cross section of the blood vessel. Accordingly, the flow rate of the blood flow may approximately be obtained by multiplying the velocity of the blood flow by a given coefficient. Further, if the ultrasonic beam for Doppler signal detection is so controlled as to scan the entire length of the vessel, it is possible to obtain a distribution of the blood flow over the entire length of the blood flow. In this case, the order of radiation of the ultrasonic beam for Doppler signal detection is IID(j−10), IID(j−10), . . . , IID(j−10); IID(j−9), IID(j−9), . . . , IID(j−9); IID(j−8), . . . ; IID(j−7), . . . . ; . . . ; IIDj, . . . ; IID(j+1), . . . ; . . . ; IID(j+10), . . . . ; . . . . In this way, the same position is scanned 64 times by the ultrasonic beam for Doppler signal detection. Then, the transducers to be driven are shifted by one transducer, and another position is scanned 64 times by the ultrasonic beam.

Since the blood flow in the artery is synchronized with the heart beat, accurate data can be obtained if the ulstrasonic beam for Doppler signal detection is shifted in synchronism with the heart beat. Further, if the B mode tomogram 6b of one frame or the B mode tomograms 6a and 6b of one frame is obtained every time the ultrasonic beam for Doppler signal detection is shifted in synchronism with the heart beat and the information obtained are stored in the DSC 21, it can check the blood vessel where the ultrasonic beam passes, providing a correct blood flow measurement.

As described above, in the ultrasonic diagnosing apparatus of the present invention, both the longitudinal and cross sections of the blood vessel are displayed simultaneously so that the angle of the blood vessel with respect to the ultrasonic beam for Doppler signal detection can be meaasured accurately thereby to provide a correct blood flow velocity and flow rate.

According to the invention, further, the same transducer array is used for radiating the ultrasonic beam to obtain the B mode tomogram and for radiating the ultrasonic beam for Doppler signal detection. This indicates that the velocity and flow rate of the blood flow at a desired position of the blood vessel can be accurately measured. Therefore, the ultrasonic diagnosing apparatus of the invention is free from an measurement error produced when separate transducer arrays are used for the same purpose. The ultrasonic diagnosing apparatus of the present invention can transmit the ultrasonic beam for detecting the Doppler signal. Therefore, by disposing the probe on a surface of a human body and displaying the B mode tomograms of the longitudinal and cross sections of a specified location of the blood vessel on the display device, the velocity and flow rate of the blood flow can automatically be measured and displayed on real time. Further, it is confirmed that the flow rate is the one at the given location in the blood vessel actually being displayed in the form of a B mode tomogram on the screen of the display device. This insures the measurement of a correct flow rate.

What is claimed is:

1. An ultrasonic diagnosing apparatus comprising:
    a first transducer array having a plurality of ultrasonic transducers arranged in a given direction for transmitting an ultrasonic beam into a tissue of a human body and for receiving the ultrasonic echo reflected from the tissue;
    a second transducer array having a plurality of ultrasonic transducers, for transmitting an ultrasonic beam into the tissue and receiving the ultrasonic echo reflected from the tissue, arrayed in a direction orthogonal to the direction of an array of the transducers in said first transducer array and arranged at an acute angle with respect to said first transducer array in a direction along which the ultrasonic beam of said first transducer array is transmitted and the ultrasonic echo is received;
    a first signal processing circuit for processing the ultrasonic echo received by said first transducer array to produce an output signal corresponding to tomogram information of the tissue;
    a second signal processing circuit for processing the ultrasonic echo received by said second transducer array to produce an output signal corresponding to a velocity of a blood flow in the tissue;
    first display means for displaying a tomogram based on the output signal of said first signal processing circuit; and
    second display means for displaying blood flow information based on the output signal of said second signal processing circuit.

2. An ultrasonic diagnosing apparatus according to claim 1, where said first signal processing circuit includes:
    means for amplifying a signal corresponding to the ultrasonic echo received by said first transducer array;
    means for amplitude detecting the output signal of said amplifying means;
    video amplifying means for amplifying the output signal of said amplitude detecting means; and
    scanning converting means for storing the output signal of said video amplifying means.

3. An ultrasonic diagnosing apparatus according to claim 1, wherein said second signal processing circuit includes:
    means for amplifying a signal corresponding the ultrasonic echo received by said second transducer array;
    means for phase detecting the output signal of said amplifying means;
    a detecting circuit for detecting a velocity of a blood flow by receiving the output signal of said phase detecting means; and
    a circuit for detecting a flow rate of the blood flow by receiving the output signal representative of the velocity of blood flow of said blood flow velocity detecting circuit.

4. An ultrasonic diagnosing apparatus according to claim 3, wherein said blood flow velocity detecting circuit includes:
    analog-to-digital (A/D) converting means for effecting an A/D conversion of the output signal of said phase detecting means;
    a random access memory stored with data to be compased with the output signal of said A/D converting means;
    means for comparing the output signal of said A/D converting means with the data stored in said random access memory;
    a circuit for integrating the output signal of said comparing means; and
    digital-to-digital (D/A) converting means for effecting a D/A conversion of the output signal of said integrating circuit.

5. An ultrasonic diagnosing apparatus according to claim 4, wherein said integrating circuit includes:
    an adder for adding the output signal of said comparing means to the output signal of a coefficient multiplier;
    a random access memory for storing the output signal of said adder; and
    said coefficient multiplier for multiplying the output signal of said random access memory by a predetermined coefficient.

6. An ultrasonic diagnosing apparatus according to claim 3, wherein said blood flow rate detecting circuit includes:
    an integrating circuit for integrating the output signal of said blood flow velocity detecting circuit;
    an adder for adding the output signals of said integrating circuit; and
    a coefficient multiplying circuit for multiplying the output signal of said adder by a predetermined coefficient.

* * * * *